United States Patent
Cheng et al.

(10) Patent No.: US 9,372,172 B2
(45) Date of Patent: *Jun. 21, 2016

(54) SYSTEMS AND METHODS FOR DETECTING PARTIAL DISCHARGE IN ELECTRICAL COMPONENTS

(71) Applicant: ROCKWELL AUTOMATION TECHNOLOGIES, INC., Mayfield Heights, OH (US)

(72) Inventors: Zhongyuan Cheng, Cambridge (CA); Catalin F. Gemanaru, Elmira (CA); Navid Reza Zargari, Cambridge (CA); Robert N. Bickford, Milton (CA)

(73) Assignee: Rockwell Automation Technologies, Inc., Mayfield Heights, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,540

(22) Filed: Jan. 28, 2015

(65) Prior Publication Data

US 2015/0137827 A1 May 21, 2015

Related U.S. Application Data

(63) Continuation of application No. 14/043,652, filed on Oct. 1, 2013.

(51) Int. Cl.
*G01R 31/08* (2006.01)
*G01N 29/00* (2006.01)
(Continued)

(52) U.S. Cl.
CPC .............. *G01N 29/00* (2013.01); *G01N 29/14* (2013.01); *G01R 31/1209* (2013.01); *G01R 31/1272* (2013.01); *G01N 2291/2697* (2013.01); *G01R 31/027* (2013.01); *G01R 31/028* (2013.01)

(58) Field of Classification Search
CPC ...... G01R 1/07; G01R 31/024; G01R 31/027; G01R 31/12; G01R 31/1272; G01R 29/02; G01R 31/028; G01R 31/1227; G01R 31/346; G01N 29/00; G01N 29/348; G01N 21/88; G01N 21/952; G01D 18/00; G01S 3/80; G01S 5/18

See application file for complete search history.

(56) References Cited

U.S. PATENT DOCUMENTS 3,728,619 A * 4/1973 Harrold et al. ............... 324/536
(Continued)

FOREIGN PATENT DOCUMENTS

DE     3816047 A1    11/1989
(Continued)

OTHER PUBLICATIONS

Extended European Search Report Mailed Mar. 2, 2015. Zargari et al: "Modified Optical re Sensor for PD Detection in High-Voltage Power Equipment", Jun. 16, 1996.
(Continued)

*Primary Examiner* — Vinh Nguyen
(74) *Attorney, Agent, or Firm* — Fletcher Yoder, P.C.

(57) ABSTRACT

A system for detecting partial discharge in electrical components may include a control system that may operate a drive in an industrial automation system. The industrial automation system may include the electrical components being analyzed for partial discharge. The system may also include one or more acoustic sensors that may detect one or more acoustic waveforms generated within at least one of the electrical components. The system may also include a monitoring system that may receive the acoustic waveforms from the acoustic sensors and determine whether the one electrical component is experiencing partial discharge based on the acoustic waveforms. The monitoring system may then send a notification to the control system when the one electrical component is determined to be experiencing partial discharge, such that the notification indicates that the one electrical component is experiencing partial discharge.

20 Claims, 3 Drawing Sheets

(51) Int. Cl.
*G01R 31/12* (2006.01)
*G01N 29/14* (2006.01)
*G01R 31/02* (2006.01)

(56) References Cited

U.S. PATENT DOCUMENTS

| | | | |
|---|---|---|---|
| 5,530,366 | A | 6/1996 | Nasrallah |
| 6,340,890 | B1* | 1/2002 | Bengtsson et al. ............ 324/536 |
| 6,774,639 | B1 | 8/2004 | Unsworth |
| 7,161,873 | B2 | 1/2007 | Kuppuswamy et al. |
| 7,737,652 | B2 | 6/2010 | Schwesig |
| 8,149,587 | B2 | 4/2012 | Baran et al. |
| 2005/0243649 | A1 | 11/2005 | Kuppuswamy et al. |
| 2007/0229018 | A1 | 10/2007 | Mitchell et al. |
| 2008/0061721 | A1 | 3/2008 | Schwesig |
| 2014/0172327 | A1* | 6/2014 | Zhou ..................... G01R 31/027 702/58 |
| 2014/0191767 | A1* | 7/2014 | Zhou ..................... G01R 31/04 324/538 |
| 2015/0091598 | A1* | 4/2015 | Han .................... G01R 31/1227 324/754.25 |

FOREIGN PATENT DOCUMENTS

| | | |
|---|---|---|
| EP | 2579056 A2 | 4/2013 |
| EP | 2814153 A2 | 12/2014 |
| JP | S5780572 A | 5/1982 |
| JP | S60211812 A | 10/1985 |
| JP | S62194475 A | 8/1987 |
| JP | H01145585 A | 6/1989 |
| JP | H08320356 A | 12/1996 |
| JP | 2008051566 A | 6/2008 |
| WO | 9428566 A1 | 12/1994 |
| WO | 9742742 A1 | 7/1997 |
| WO | 0218963 A1 | 3/2002 |
| WO | 03044516 A1 | 5/2003 |

OTHER PUBLICATIONS

Unsworth et al: "Evaluation of Novel On-Line Remote Partial Discharge Monitor for High Voltage Power Transformers During Operation", Jun. 14, 1999.

Doble, Dielectric Fault Analyzer (Dfa100) Instrument in-Service Testing of Sf6 Filled Dead Tank Circuit Breakers Using the Acoustic Emission Diagnostic Technique, pp. 1-5. http://www.doble.com/content/products/1_DFA100_Application_Note_-_Dead_Tank_Breaker.pdf (Accessed Oct. 1, 2013).

Reid, Richard, Corona and Partial Discharge Detection by the Charge-Release Method; Oct. 16, 1975, pp. 1-27, N.Y., N.Y.

Doble Engineering Company, DFA100 Dielectric Fault Analyzer, pp. 1-2. http://www.doble.com/content/products/DFA100_Brochure_03-08.pdf (Accessed Oct. 1, 2013).

Lundgaard, L. E., Norwegian Electric Power Research Institute (EFI), Partial Discharge—Part XIV: Acoustic Partial Discharge Detection—Practical Application; Sep./Oct. 1992, pp. 34-43, vol. 8, No. 5, IEEE Electrical Insulation Magazine.

Boggs, Steven A., Underground Systems, Inc., Partial Discharge: Overview and Signal Generation, Jul./Aug. 1990, pp. 33-39, vol. 6, No. 4, IEEE Electrical Insulation Magazine.

Boggs, Steven A., Underground Systems, Inc., Partial Discharge—Part II: Detection Sensitivity, Sep./Oct. 1990, pp. 35-34, vol. 6, No. 5, IEEE Electrical Insulation Magazine.

Boggs, Steven A., Underground Systems, Inc., Partial Discharge—Part III: Cavity-Induced PD in Solid Dielectrics, Nov./Dec. 1990, pp. 11-20, vol. 6, No. 6, IEEE Electrical Insulation Magazine.

Steiner, J. P., Biddle Instruments, Partial Discharge—Part IV: Commercial PD Testing, Jan./Feb. 1991, pp. 20-33, vol. 7, No. 1, IEEE Electrical Insulation Magazine.

Lundgaard, L. E., Norwegian Electric Power Research Institute (EFI), Partial Discharge—Part XIII: Acoustic Partial Discharge Detection-Fundamental Considerations, Jul./Aug. 1992, pp. 25-31, vol. 8, No. 4, IEEE Electrical Insulation Magazine.

* cited by examiner

SYSTEMS AND METHODS FOR DETECTING PARTIAL DISCHARGE IN ELECTRICAL COMPONENTS

CROSS REFERENCE TO RELATED APPLICATIONS

This application is a Continuation of U.S. patent application Ser. No. 14/043,652, entitled "SYSTEMS AND METHODS FOR DETECTING PARTIAL DISCHARGE IN ELECTRICAL COMPONENTS", filed on Oct. 1, 2013, which is herein incorporated by reference.

BACKGROUND

Embodiments of the present disclosure relate generally to systems and methods for predicting when electrical components in industrial automation systems may become inoperable. More specifically, the present disclosure relates to detecting partial discharge in electrical components used in industrial automation systems.

Industrial automation systems may employ various types of electronic devices such as an alternating current (AC) drive to provide a controllable AC voltage to various devices within an industrial automation system. The AC drive may receive AC voltage from an AC voltage source and convert the received AC voltage into direct current (DC) voltage using a rectifier. The AC drive may then convert the DC voltage into a controllable AC voltage using an inverter. In some cases, a regenerative AC drive may provide regenerated power back to a grid or to an AC voltage source from the inverter.

In addition to the AC drive, the industrial automation system may include electrical components, such as inductor-capacitor-inductor (LCL) filters, line capacitors, transformers, and the like to enable the industrial automation system to operate. Unfortunately, as the electrical components are used through the life of the industrial automation system, it is now recognized that the electrical components show little degradation characteristics before becoming inoperable. Accordingly, it is now recognized that improved systems and methods for detecting when an electrical component may become inoperable prior to actually becoming inoperable are desirable.

BRIEF DESCRIPTION

In one embodiment, a system for detecting partial discharge in electrical components may include a control system that may operate a drive in an industrial automation system. The industrial automation system may include the electrical components being analyzed for partial discharge. The electrical components may include any electrical device that may be electrically coupled to the drive. The system may also include one or more acoustic sensors that may detect one or more acoustic waveforms generated within at least one of the electrical components. The system may also include a monitoring system that may receive the acoustic waveforms from the acoustic sensors and determine whether the one electrical component is experiencing partial discharge based on the acoustic waveforms. The monitoring system may then send a notification to the control system when the one electrical component is determined to be experiencing partial discharge, such that the notification indicates that the one electrical component is experiencing partial discharge.

In another embodiment, a method for protecting devices in an industrial automation system may include receiving a first signal indicating that one or more inputs associated with a drive are energized. The method may then include receiving one or more acoustic waveforms from one or more acoustic sensors physically disposed on an electrical component after one or more transient voltages at the inputs have settled. Here, the electrical component may be directly or indirectly electrically coupled to the drive. The method may then include determining whether the electrical component is experiencing partial discharge based on the acoustic waveforms and sending a second signal to one or more control systems when the electrical component is experiencing partial discharge. The second signal may cause one or more electrical components in the industrial automation system to electrically disconnect from the drive.

In yet another embodiment, a monitoring control system may include a communication component that may communicate with one or more acoustic sensors coupled to an electrical component in an industrial automation system and a drive control system that may operate a drive in the industrial automation system. The monitoring control system may also include a processor that may receive one or more acoustic waveforms from the acoustic sensors and determine whether the electrical component is experiencing partial discharge based on the acoustic waveforms. The monitoring control system may then send a notification to the drive control system when the electrical component is determined to be experiencing partial discharge.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

Embodiments of the present disclosure are generally directed towards a partial discharge (PD) detection system that may use acoustic sensors to predict when an electrical component may become inoperable. In one embodiment, one or more acoustic sensors may be disposed on the housing of an electrical component, such as a capacitor, to monitor acoustic waveforms being generated within the electrical component. That is, when the electrical component is energized at its nominal or rated voltage, the one or more acoustic sensors may receive the acoustic waveforms being produced from within the electrical component. In certain embodiments, a partial discharge (PD) monitoring system may then receive the acoustic waveforms and determine whether the electrical component is experiencing partial discharge based on the acoustic waveforms.

If the PD monitoring system detects partial discharge within the electrical component, the PD monitoring system may send a message to an industrial automation drive control system indicating that the electrical component is experiencing partial discharge and may soon become inoperable. Upon receiving this message from the PD monitoring system, the industrial automation drive control system may perform a variety of actions based on the electrical component soon becoming inoperable. For instance, the industrial automation drive control system may send a signal to downstream devices to power down or electrically isolate themselves from the rest of the industrial automation system, send a message to the appropriate personnel indicating that the electrical component may soon become inoperable, send a signal to various annunciators to request maintenance for the industrial automation system, and so forth. By monitoring the presence of partial discharge while electrical components are installed within the industrial automation system, the industrial automation drive control system may ensure that the industrial automation system operates effectively and safely by preventing the industrial automation system from being online when an electrical component becomes inoperable (i.e., fails).

Figure 1:
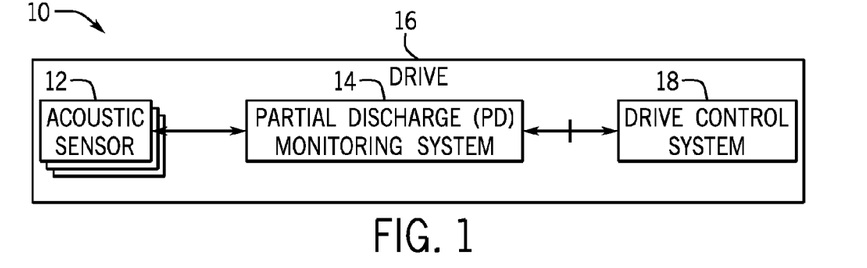
FIG. 1 illustrates a block diagram of a partial discharge (PD) detection system, in accordance with embodiments presented herein.

By way of introduction, FIG. 1 illustrates a block diagram of a partial discharge (PD) detection system 10. The PD detection system 10 may include one or more acoustic sensors 12, a partial discharge (PD) monitoring system 14, an industrial automation drive 16, and a drive control system 18. As shown in FIG. 1, in certain embodiments, the acoustic sensors 12, an electronic component being monitored by the acoustic sensors 12, and the PD monitoring system 14 may be integral to the drive 16. That is, the acoustic sensors 12, the electronic component being monitored by the acoustic sensors 12, and the PD monitoring system 14 may be physically enclosed within the walls or enclosure of the drive 16. However, it should be noted, that the acoustic sensors 12, the electronic component being monitored by the acoustic sensors 12, and the PD monitoring system 14 may also be located outside of the enclosure of the drive 16.

The acoustic sensor 12 may be any type of sensor that may be capable of detecting raw acoustic data (i.e., acoustic waveforms). For instance, the acoustic sensor 12 may include an ultrasound sensor capable of detecting acoustic waveforms at frequencies up to at least 300 kHz. In certain embodiments, the acoustic sensor 12 may be physically coupled to an electrical component such as a transformer, a capacitor, or the like. In one embodiment, the acoustic sensor 12 may be physically coupled to the electrical component in the middle of a flat surface of the electrical component. The acoustic sensor 12 may also be placed on a surface of the electrical component that has the largest surface area. Wherever the acoustic sensor 12 is place, the acoustic sensor 12 may detect or sense the acoustic waveforms being generated from within the electrical component after the acoustic waveforms travel from the source of the partial discharge to the same acoustic sensor 12. By placing the acoustic sensor 12 in the center of the surface, the acoustic sensor 12 may more effectively detect acoustic waveforms that may be generated from any corner of the electrical component. In one embodiment, the acoustic sensor 12 may be attached to the electrical component via a magnetic holder.

Generally, partial discharge should not exist in any electrical component. The existence of any partial discharge in an electrical component is typically indicative of dielectric breakdown of the insulation within the electrical component. Moreover, once partial discharge becomes present in an electrical component, the electrical component typically fails or becomes inoperable shortly thereafter. As such, electrical component manufacturers usually perform partial discharge tests prior to completing the manufacturing process for the electrical component.

Conventional partial discharge testing techniques include electrical partial discharge testing, which may involve coupling a high voltage source to an isolated (i.e., not coupled to any other component) electrical component and determining whether any electric arcing is occurring, any leakage current is detected, or the like. However, once an electrical component is electrically coupled to another component or system, such as the industrial automation drive 16, electrically testing the electrical component for partial discharge becomes increasingly difficult. That is, since the electrical component is no longer isolated when coupled to another component or system, electrical partial discharge testing techniques becomes difficult since the high voltage provided for the testing will be coupled to the additional component or system, as opposed to just the single electrical component.

Keeping the foregoing in mind, the acoustic sensor 12 may detect partial discharge in an electrical component even when the electrical component is electrically coupled to another device, system, or the like based on the acoustic waveforms it detects or senses. That is, if the acoustic sensor 12 detects or senses acoustic waveforms being generated from within the electrical component, the acoustic sensor 12 may send raw acoustic data that includes the detected acoustic waveforms to the PD monitoring system 14. As such, the PD monitoring system 14 may be communicatively coupled to the acoustic sensor 12 via a wired or wireless connection. After receiving the raw acoustic data, the PD monitoring system 14 may analyze the raw acoustic data to determine whether the raw acoustic data indicates that the electrical component physically coupled to the acoustic sensor 12 is experiencing partial discharge.

Generally, partial discharge occurs inside an electrical component after the insulation inside the electrical component degrades such that the space between two conductors may not be sufficient to prevent electrical arcing or the like. During a partial discharge incident, an amount of energy may be released due to the partial discharge. This release of energy may be the source of the acoustic waveforms detected by the acoustic sensors 12 and analyzed by the PD monitoring system 14. In one embodiment, the PD monitoring system 14 may determine whether the detected acoustic waveforms indicate that the electrical component is experiencing partial discharge by analyzing the acoustic waveforms in the frequency range between 20 kHz and 300 kHz.

In addition to receiving the detected acoustic waveforms, the PD monitoring system 14 may receive a signal that corresponds to a voltage signal being applied to the electrical component. Using the voltage signal, which may be an alternating current (AC) sine wave, the PD monitoring system 14 may determine whether the nature of the acoustic waveforms is periodic. That is, the PD monitoring system 14 may determine whether the detected acoustic waveforms are synchronized with the peak of the voltage signal being applied to the electrical component. In certain embodiments, partial discharge may be periodic and may be more likely to occur during the peak voltage levels of the voltage signal being applied to the monitored electrical component. As such, the PD monitoring system 14 may use the voltage signal along with the detected acoustic waveforms to determine whether the electrical component being monitored is experiencing partial discharge.

After determining whether the detected acoustic waveforms indicate that the electrical component is experiencing partial discharge, the PD monitoring system 14 may send a notification or the like indicating the same to the industrial automation drive 16. In one embodiment, the PD monitoring system 14 may send the notification to the drive control system 18. Generally, the drive control system 18 may include certain logic or computer-executable code that may control the operation of the drive 16. As such, the drive control system 18 may monitor various conditions that are associated with the drive 16 and may perform various actions based on the monitored conditions. For instance, after the drive control system 18 receives the notification indicating that the electrical component is experiencing partial discharge, the drive control system 18 may notify a user of the partial discharge situation, stop operating the drive 16, send one or more signals to upstream or downstream devices to power down, or the like. Additional details with regard to actions that may be taken by the drive control system 18 will be discussed in greater detail with reference to FIGS. 6 and 7 below.

Figure 2:
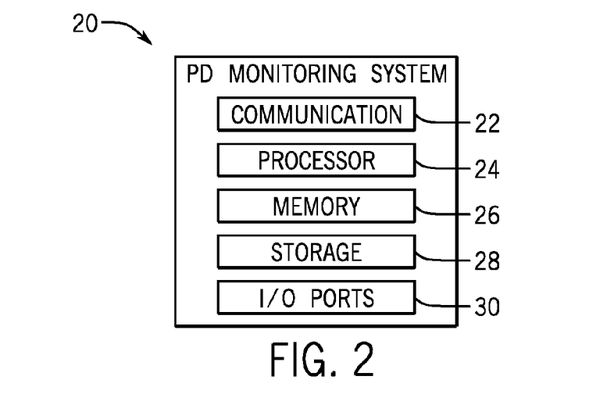
FIG. 2 illustrates a block diagram of a partial discharge (PD) monitoring system that may be part of the PD detection system of FIG. 1, in accordance with embodiments presented herein.

To effectively enable the PD monitoring system 14 and the drive control system 18 to perform the operations described above, the PD monitoring system 14 and the drive control system 18 may include various components that may receive data, process data, communicate data, store data, and so forth. FIG. 2 depicts a detailed block diagram 20 of the PD monitoring system 14 and some of the components that may enable the PD monitoring system to perform the techniques described herein. Although FIG. 2 illustrates components that may be part of the PD monitoring system 14, it should be noted that the drive control system 18 may also include the components depicted in FIG. 2. As shown in the figure, the PD monitoring system 14 may include a communication component 22, a processor 24, a memory 26, a storage 28, input/output (I/O) ports 30, and the like. The communication component 22 may be a wireless or wired communication component that may facilitate communication between the acoustic sensor 12, the drive control system 18, other control systems, and the like. The processor 24 may be any type of computer processor or microprocessor capable of executing computer-executable code. The memory 26 and the storage 28 may be any suitable articles of manufacture that can serve as media to store processor-executable code, data, or the like. These articles of manufacture may represent non-transitory computer-readable media (i.e., any suitable form of memory or storage) that may store the processor-executable code used by the processor 24 to determine whether the electrical component physically coupled to the acoustic sensor 12, wherein non-transitory merely indicates that the media is tangible and not a signal.

Figure 3:
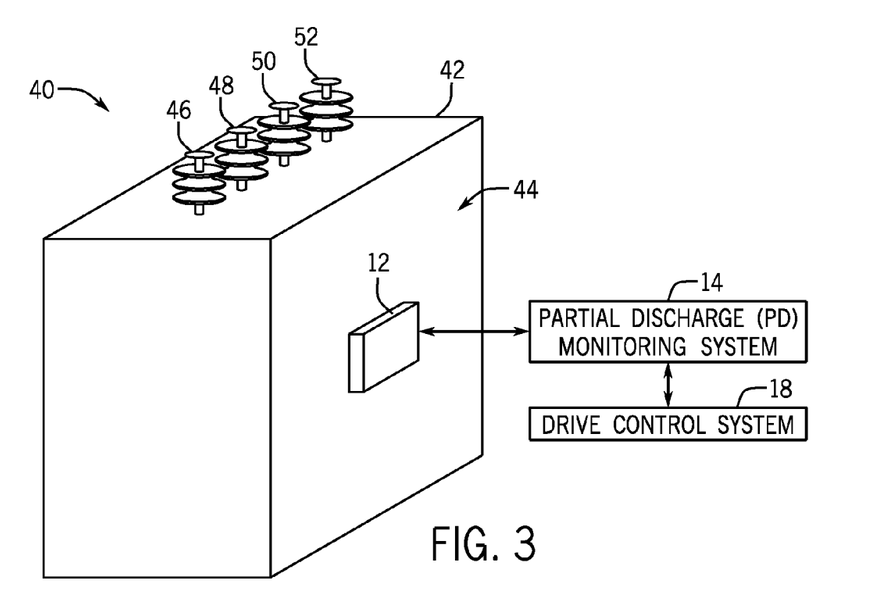
FIG. 3 illustrates a perspective view of an acoustic sensor coupled to a three-phase capacitor, in accordance with embodiments presented herein.

In one embodiment, the acoustic sensor 12 may be physically attached to an electrical component, such as a capacitor. For instance, FIG. 3 illustrates a perspective view 40 of the acoustic sensor 12 physically coupled to a surface of a three-phase capacitor 42. As shown in FIG. 3, the acoustic sensor 12 may be physically disposed on a side of the three-phase capacitor 42 that has the largest surface area 44. Generally, the acoustic sensor 12 may more effectively monitor the acoustic waveforms within the three-phase capacitor 42 when placed in the center of a respective surface area. Once the acoustic sensor 12 receives acoustic waveforms generated from within the three-phase capacitor 42, the acoustic sensor 12 may send the corresponding raw acoustic data to the PD monitoring system 14. The PD monitoring system 14 may then analyze the raw acoustic data as discussed above. After analyzing the raw acoustic data, the PD monitoring system 14 may send the results of the analysis to the drive control system 18, which may perform various actions based on the results.

Figure 4:
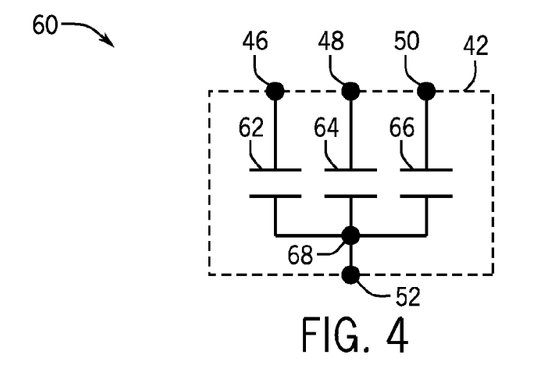
FIG. 4 illustrates an electrical circuit diagram of the three-phase capacitor of FIG. 3, in accordance with embodiments presented herein.

The three-phase capacitor 42 may include four terminals 46, 48, 50, 52, such that three of the terminals (e.g., 46, 48, 50) may be electrically coupled to a respective capacitor, while the fourth terminal (e.g., 52) may be electrically coupled to a neutral node where the opposite terminals of three of the terminals (e.g., 46, 48, 50) may be electrically coupled together. To better illustrate the electrical connections of the three capacitors in the three-phase capacitor 42, FIG. 4 illustrates an electrical circuit diagram 60 that corresponds to the three-phase capacitor 42 described above. As illustrated in FIG. 4, the three-phase capacitor 42 may include three capacitors 62, 64, 66 that may be electrically coupled to terminals 46, 48, 50, respectively. Moreover, each capacitor 62, 64, 66 may also be electrically coupled together to form a neutral node 68, which may be electrically coupled the fourth terminal 52. Although FIGS. 3 and 4 depict the three-phase capacitor 42 being monitored by the acoustic sensor 12, it should be noted that the three-phase capacitor 42 is provided as one example, and the electrical component being monitored by the acoustic sensor 12 may include any type of electrical component such as a transformer, an inductor, and the like.

Figure 5:
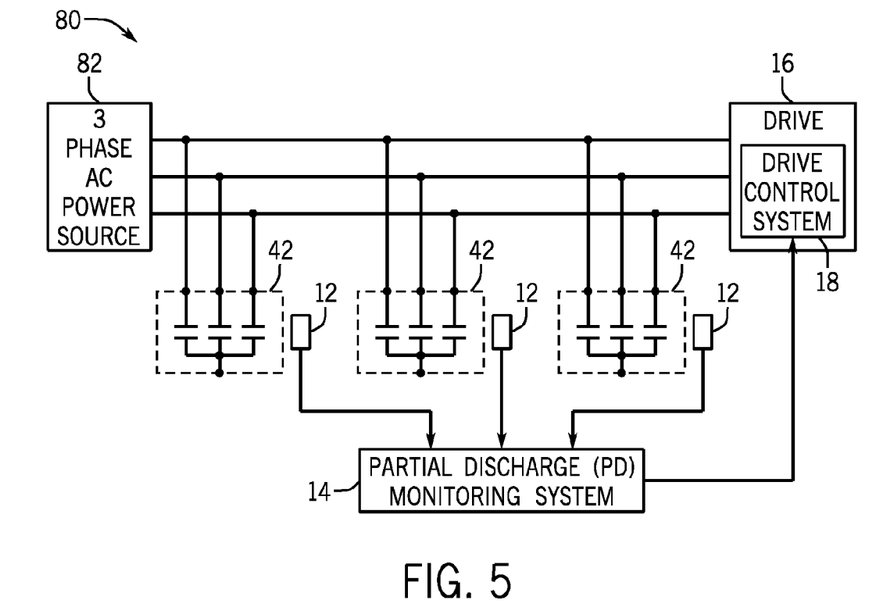
FIG. 5 illustrates a block diagram of an example three-phase industrial automation drive system employing the PD detection system of FIG. 1, in accordance with embodiments presented herein.

In certain embodiments, the three-phase capacitor 42 may be used in a three-phase industrial automation drive system as part of a line capacitor, an inductor-capacitor-inductor (LCL) filter, an inductor-capacitor (LC) filter, or the like. FIG. 5 illustrates an example three-phase industrial automation drive system 80 that may use the PD monitoring system 14 to determine whether an electrical component within the three-phase industrial automation drive system 80 is experiencing partial discharge. Referring now to FIG. 5, the three-phase industrial automation drive system 80 may include a three-phase AC power source 82, a number of three-phase capacitors 42, the acoustic sensors 12, the PD monitoring system 14, the drive 16, and the drive control system 18. In one embodiment, each three-phase capacitor 42 may have one or more acoustic sensors 12 physically disposed on the surface of a respective three-phase capacitor 42. As such, the acoustic sensors 12 may receive acoustic waveforms that may have originated from within the respective three-phase capacitor 42. As mentioned above, the acoustic sensors 12 may send raw acoustic data to the PD monitoring system 14 to determine whether the raw acoustic data is indicative of partial discharge occurring within the respective three-phase capacitor 42. In one embodiment, the acoustic sensor 12 may send identification information in addition to the raw acoustic data, such that the PD monitoring system 14 may identify which three-phase capacitor 42 corresponds to the received raw acoustic data. Once the PD monitoring system 14 determines whether partial discharge is occurring in one or more of the three-phase capacitors 42 in the three-phase industrial automation drive system 80, the PD monitoring system 14 may send the drive control system 18 a message or notification indicating that partial discharge occurring within the respective three-phase capacitor 42.

Figure 6:
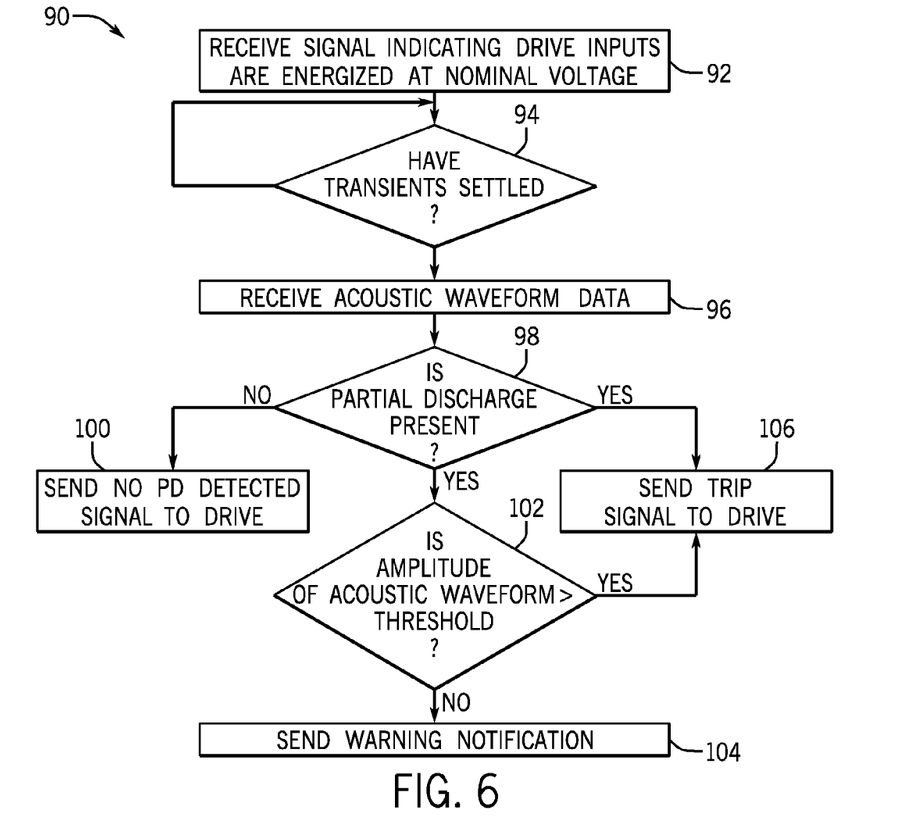
FIG. 6 illustrates a flow chart of a method for determining whether a component in an industrial automation system is experiencing partial discharge using the PD detection system of FIG. 1, in accordance with embodiments presented herein.

In certain embodiments, the drive control system 18 may initiate a process for determining whether an electrical component, such as the three-phase capacitor 42, is experiencing partial discharge. For instance, the drive control system 18 may send a command or signal to the PD monitoring system 14 to initiate a process for determining whether an electrical component in an industrial automation system is experiencing partial discharge. FIG. 6 illustrates a flow chart of this process (i.e., method 90) that the PD monitoring system 14 may employ for determining whether an electrical component in an industrial automation system is experiencing partial discharge while the electrical component is part of or coupled to the industrial automation system.

Referring now to FIG. 6, at block 92, the PD monitoring system 14 may receive a signal indicating that the inputs to the drive 16 have been energized at a nominal voltage. In one embodiment, the method 90 may be performed when the drive 16 is operating in a ready mode. The drive 16 may be operating in ready mode when the inputs of the drive 16 are energized but the drive 16 has not started conducting current to its load. As such, the signal indicating that the inputs to the drive 16 have been energized may also include voltage waveforms that correspond to the voltage being applied to the inputs of the drive 16.

At block 94, the PD monitoring system 14 may determine whether the transient voltages of the inputs of the drive 16 have settled. That is, the PD monitoring system 14 may analyze the voltage waveforms that correspond to the voltage being applied to the inputs of the drive 16 to determine whether the transients in the voltage waveforms have settled. If the transient voltages have not settled, the PD monitoring system 14 may return to block 94 and continue monitoring the transient voltages until they settle. After the transient voltages settle, the PD monitoring system 14 may proceed to block 96 and receive the raw acoustic data from the acoustic sensors 12, which may be physically coupled to the electrical component being tested.

At block 98, the PD monitoring system 14 may determine whether partial discharge is present in the raw acoustic data. The PD monitoring system 14 may determine whether partial discharge is present in the raw acoustic data by analyzing the acoustic waveforms in the raw acoustic data to determine whether the acoustic waveforms include an acoustic signature that corresponds to partial discharge. As mentioned above, the PD monitoring system 14 may determine whether the detected acoustic waveforms indicate that the electrical component is experiencing partial discharge based on whether acoustic waveforms exist between 20 kHz and 300 kHz. Additionally, the PD monitoring system 14 may determine whether the nature of the acoustic waveforms is periodic and whether the acoustic waveforms are synchronized with the peak of the input voltage applied to the electrical component.

If, at block 98, the PD monitoring system 14 determines that partial discharge is not present in the electrical component, the PD monitoring system 14 may proceed to block 100 and send a signal to the drive control system 18 that indicates that no partial discharge is detected in the electrical component. If, however, at block 98, the PD monitoring system 14 determines that partial discharge is present in the electrical component, the PD monitoring system 14 may proceed to block 102.

At block 102, the PD monitoring system 14 may determine whether the amplitude of the detected acoustic waveform is greater than some threshold. Alternatively, the PD monitoring system 14 may determine whether the rising slope of the detected acoustic waveform is greater than some threshold. If the amplitude or the rising slope is not greater than the threshold, the PD monitoring system 14 may proceed to block 104 and send a warning notification to the drive control system 18. The warning notification may indicate that the electrical component being monitored may be experiencing partial discharge and that the electronic component may become inoperable sometime in the future.

If, however, at block 102, the PD monitoring system 14 determines that the amplitude or the rising slope of the acoustic waveforms is greater than the threshold, the PD monitoring system 14 may send a trip signal to the drive control system 18. The trip signal may indicate that the electrical component is experiencing partial discharge and may soon become inoperable. As such, the trip signal may cause the drive control system 18 to stop operating the drive 16, send a signal to one or more upstream or downstream devices to disconnect from the system or power down, or the like. Referring back to block 98, in certain embodiments, if the PD monitoring system 14 determines that partial discharge is present in the electrical component, the PD monitoring system 14 may proceed to block 106 and send the trip signal to the drive control system 18 as described above. As such, the PD monitoring system 14 may forego sending the warning notification to the drive control system 18.

In one embodiment, the method 90 may be performed periodically to determine whether the electrical component will become inoperable in the near future. As such, the drive control system 18 may continuously monitor the integrity of a number of electronic components within the industrial automation system.

In addition to performing the test for partial discharge while the drive 16 is in ready mode, the drive control system 18 may also test whether an electrical component is experiencing partial discharge at scheduled maintenance intervals. For example, FIG. 7 illustrates a flow chart of a method 110 for determining, at scheduled maintenance times, whether an electrical component, such as the three-phase capacitor 42, is experiencing partial discharge.

Figure 7:
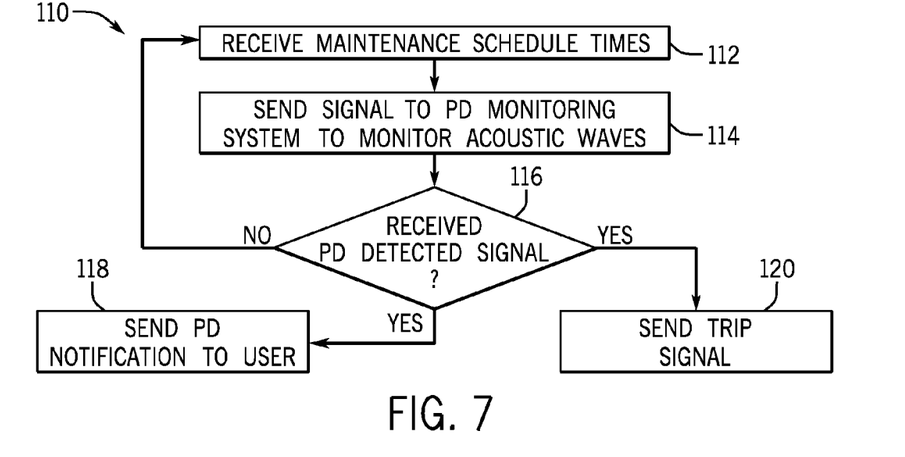
FIG. 7 illustrates a flow chart of a method for determining, at scheduled maintenance times, whether an electrical component is experiencing partial discharge using the PD detection system of FIG. 1, in accordance with embodiments presented herein.

Referring to FIG. 7, at block 112, the drive control system 18 may receive a maintenance schedule with one or more times at which various components in the industrial automation system may be scheduled for inspection, maintenance, or the like. After receiving the maintenance schedule, the drive control system 18 may, at block 114, send a signal to the PD monitoring system 14 at each scheduled time according to the maintenance schedule. The signal may instruct the PD monitoring system 14 to monitor the acoustic waveforms received by the acoustic sensors 12 physically disposed on the electrical component. Once the PD monitoring system 14 receives the signal, the PD monitoring system 14 may determine whether the acoustic waveforms received from the acoustics sensors 12 indicate that the electrical component is experiencing partial discharge using the techniques discussed above. If the PD monitoring system 14 determines that the electrical component is experiencing partial discharge, the PD monitoring system 14 may send a notification to the drive control system 18 indicating that partial discharge is occurring in the electrical component.

Keeping this in mind, at block 116, the drive control system 18 may determine whether it received the notification indicating that partial discharge is occurring in the electrical component. If the drive control system 18 receives the notification, the drive control system 18 may proceed to block 118. At block 118, the drive control system 18 sends a notification to a user of the drive control system 18 indicating that the electrical component is experiencing partial discharge. In another embodiment, if the drive control system 18 receives the notification, the drive control system 18 may proceed to block 120 and send a trip signal to upstream and/or downstream components. As mentioned above, the trip signal may cause the upstream and/or downstream components to power down or remove them from the industrial automation system, thereby electrically isolating themselves from the electronic component experiencing partial discharge. In one embodiment, if the drive control system 18 receives the notification, the drive control system 18 may power down or electrically isolate itself from the industrial automation system to protect the other components in the industrial automation system.

Referring back to block 116, if the drive control system 18 does not receive the notification indicating that partial discharge is occurring in the electrical component, the drive control system 18 may return to block 112 and repeat the method 110. By testing electrical components for partial discharge at scheduled maintenance intervals, the drive control system 18 may anticipate when an electrical component may soon fail. As such, the drive control system 18 may notify the appropriate personnel to ensure that the faulty electrical component is replaced, such that the industrial automation system may operate more efficiently.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system, comprising:
a control system configured to operate a drive in an industrial automation system, wherein the industrial automation system comprises one or more electrical components electrically coupled to the drive, and wherein the drive comprises a rectifier configured to convert an alternating current (AC) voltage into a direct current (DC) voltage and an inverter configured to convert the DC voltage into a controllable AC voltage;
one or more acoustic sensors configured to detect one or more acoustic waveforms generated within at least one of the electrical components;
a monitoring system configured to:
  receive the acoustic waveforms from the acoustic sensors while the drive produces the controllable AC voltage;
  determine whether the at least one of the electrical components is experiencing partial discharge when one or more amplitudes of the acoustic waveforms is greater than a first threshold;
  send a notification to the control system when the at least one of the electrical components is determined to be experiencing partial discharge, wherein the notification indicates that the at least one of the electrical components is experiencing partial discharge, and wherein the control system is configured to send a trip signal to one or more devices coupled upstream or downstream from the drive after receiving the notification.

2. The system of claim 1, wherein the one or more acoustic sensors comprise one or more ultrasound sensors.

3. The system of claim 1, wherein the one or more acoustic sensors are configured to detect the acoustic waveforms at frequencies up to at least 300 kHz.

4. The system of claim 1, wherein the at least one of the electrical components comprises a capacitor.

5. The system of claim 1, wherein the one or more acoustic sensors are physically coupled to a surface of the at least one of the electrical components, wherein the surface corresponds to a largest surface area of the at least one of the electrical components.

6. The system of claim 1, wherein the monitoring system is configured to determine whether the at least one of the electrical components is experiencing partial discharge by analyzing the acoustic waveforms in a frequency range between 20 kHz and 300 kHz.

7. The system of claim 1, wherein the monitoring system is configured to determine whether the at least one of the electrical components is experiencing partial discharge by:
receiving a voltage signal that corresponds to a voltage being applied to the at least one of the electrical components; and
determining that the at least one of the electrical components is experiencing partial discharge when the acoustic waveforms are synchronized with the peak of the voltage signal.

8. The system of claim 1, wherein the control system is configured to stop an operation of the drive after receiving the notification.

9. The system of claim 1, wherein the control system is configured to send the trip signal to the devices coupled upstream or downstream from the drive when one or more rising slopes associated with the acoustic waveforms is greater than a second threshold.

10. A method, comprising:
receiving, via a processor, a schedule comprising one or more times at which an electrical component in a drive should be tested for partial discharge, wherein the electrical component is electrically coupled to the drive, wherein the drive comprises a rectifier configured to convert an alternating current (AC) voltage into a direct current (DC) voltage and an inverter configured to convert the DC voltage into a controllable AC voltage;
receiving, via the processor, one or more acoustic waveforms from one or more acoustic sensors physically disposed on the electrical component at one of the times while the drive produces the controllable AC voltage;
determining, via the processor, whether the electrical component is experiencing partial discharge based on the one or more acoustic waveforms; and
sending, via the processor, a notification when the electrical component is determined to be experiencing partial discharge, wherein the notification indicates that the electrical component is experiencing partial discharge.

11. The method of claim 10, wherein sending the notification comprises:
   determining whether one or more amplitudes of the one or more acoustic waveforms are greater than a threshold; and
   sending the notification when the one or more amplitudes are greater than the threshold.

12. The method of claim 10, wherein determining whether the electrical component is experiencing partial discharge based on the one or more acoustic waveforms comprises determining that the one or more acoustic waveforms are present in a frequency range between 20 kHz and 300 kHz.

13. The method of claim 10, wherein determining whether the electrical component is experiencing partial discharge based on the one or more acoustic waveforms comprises:
   determining that the one or more acoustic waveforms are present in a frequency range between 20 kHz and 300 kHz; and
   determining that the one or more acoustic waveforms are periodic.

14. The method of claim 10, wherein determining whether the electrical component is experiencing partial discharge based on the one or more acoustic waveforms comprises:
   receiving a voltage signal that corresponds to a voltage being applied to the electrical component;
   determining that the one or more acoustic waveforms are present in a frequency range between 20 kHz and 300 kHz; and
   determining that the one or more acoustic waveforms are periodic with respect to each peak of the voltage signal.

15. A monitoring and control system configured to detect partial discharge in an electrical component, wherein the monitoring and control system comprises:
   a communication component configured to communicate with one or more acoustic sensors coupled to the electrical component in an industrial automation system and a drive control system configured to operate a drive in the industrial automation system, wherein the electrical component is configured to electrically couple to the drive, and wherein the drive comprises a rectifier configured to convert an alternating current (AC) voltage into a direct current (DC) voltage and an inverter configured to convert the DC voltage into a controllable AC voltage; and
   a processor configured to:
      receive acoustic waveforms from the one or more acoustic sensors while the drive produces the controllable AC voltage;
      determine whether the electrical component is experiencing partial discharge based on the acoustic waveforms; and
      electrically isolate the drive when the electrical component is determined to be experiencing partial discharge.

16. The monitoring and control system of claim 15, wherein the communication component is configured to communicate with the one or more acoustic sensors and the drive control system via one or more wireless connections.

17. The monitoring and control system of claim 15, wherein the one or more acoustic sensors are physically disposed on the electrical component.

18. The monitoring and control system of claim 15, wherein at least one of the one or more acoustic sensors is physically disposed in the middle of a surface of the electrical component.

19. The monitoring and control system of claim 18, wherein the surface corresponds to a largest surface area of a housing of the electrical component.

20. The monitoring and control system of claim 15, wherein the processor is configured to receive the acoustic waveforms when the drive is in a ready mode.

* * * * *